(12) United States Patent
Pohl et al.

(10) Patent No.: US 8,496,881 B2
(45) Date of Patent: Jul. 30, 2013

(54) CHEMICAL DELIVERY ASSEMBLY

(75) Inventors: Jeffrey C. Pohl, Fort Wayne, IN (US); James A. Ritchie, Jr., Huntertown, IN (US); Jeffery A. Clark, Garrett, IN (US)

(73) Assignee: Group Dekko, Inc., Kendallville, IN (US)

( * ) Notice: Subject to any disclaimer, the term of this patent is extended or adjusted under 35 U.S.C. 154(b) by 461 days.

(21) Appl. No.: 12/797,893

(22) Filed: Jun. 10, 2010

(65) Prior Publication Data

US 2010/0247372 A1    Sep. 30, 2010

Related U.S. Application Data

(63) Continuation-in-part of application No. 12/013,736, filed on Jan. 14, 2008, now Pat. No. 7,771,665.

(60) Provisional application No. 60/884,683, filed on Jan. 12, 2007.

(51) Int. Cl.
*A61L 9/03* (2006.01)

(52) U.S. Cl.
USPC .......................................... 422/125; 422/120

(58) Field of Classification Search
USPC .................... 422/120, 125; 239/60
See application file for complete search history.

(56) References Cited

U.S. PATENT DOCUMENTS

| | | | |
|---|---|---|---|
| 1,528,640 A | 3/1925 | Tvrzicky et al. | |
| 1,609,958 A | 12/1926 | Perrault | |
| 3,976,049 A | 8/1976 | Yamashita et al. | |
| 4,163,038 A | 7/1979 | Nishimura et al. | |
| 4,171,340 A | 10/1979 | Nishimura et al. | |
| 4,228,124 A | 10/1980 | Kashihara et al. | |
| 4,544,592 A * | 10/1985 | Spector | 428/68 |
| 4,781,895 A * | 11/1988 | Spector | 422/125 |
| 5,429,271 A | 7/1995 | Porter | |
| 5,572,800 A | 11/1996 | West | |
| 6,016,138 A | 1/2000 | Harskamp et al. | |
| 6,033,212 A * | 3/2000 | Bonnema et al. | 431/344 |
| 6,309,598 B1 | 10/2001 | Tully | |
| 6,435,423 B2 | 8/2002 | Hurry et al. | |
| 6,478,440 B1 | 11/2002 | Jaworski et al. | |
| 7,081,211 B2 | 7/2006 | Li et al. | |
| 7,235,187 B2 | 6/2007 | Li et al. | |
| 2002/0141898 A1 | 10/2002 | Carlucci et al. | |
| 2002/0174863 A1 | 11/2002 | Saric et al. | |
| 2005/0224595 A1 | 10/2005 | Kuiper | |
| 2006/0039685 A1 | 2/2006 | Berrido et al. | |
| 2007/0148293 A1 | 6/2007 | Lindsay et al. | |
| 2007/0237498 A1 | 10/2007 | Helf et al. | |
| 2008/0142550 A1 | 6/2008 | Scheiber et al. | |

* cited by examiner

*Primary Examiner* — Sean E Conley
(74) *Attorney, Agent, or Firm* — Taylor IP, P.C.

(57) ABSTRACT

A chemical delivery system includes: a chemical storage device configured for emitting a volatilized chemical therefrom; a heating element which provides an exothermic chemical reaction; an at least substantially rigid housing element containing the heating element; a tray including a well, the well having an absence of a through-hole and defining a space which is slightly larger than the chemical storage device, the tray being attached to the housing element, the chemical storage device being mounted to the well, the heating element being in thermal communication with the chemical storage device via the well; a retainer attached to the well and including at least one hole configured for passing therethrough the volatilized chemical to an ambient environment, the retainer being configured for retaining the chemical storage device in the space; and a removable covering directly attached to the tray and covering the retainer and the well to thereby hermetically seal the chemical storage device within the space.

2 Claims, 8 Drawing Sheets

CHEMICAL DELIVERY ASSEMBLY

CROSS REFERENCE TO RELATED APPLICATIONS

This is a continuation-in-part of U.S. patent application Ser. No. 12/013,736, entitled "CHEMICAL DELIVERY ASSEMBLY", filed Jan. 14, 2008 now U.S. Pat. No. 7,771,665, which is incorporated herein by reference. U.S. patent application Ser. No. 12/013,736 is a non-provisional application based upon U.S. provisional patent application Ser. No. 60/884,683, entitled "SINGLE USE DISPOSABLE CHEMICAL VAPORIZING DEVICE", filed Jan. 12, 2007, which is incorporated herein by reference.

BACKGROUND OF THE INVENTION

1. Field of the Invention

The present invention relates to chemical delivery assemblies, and, more particularly, to chemical vaporizing assemblies.

2. Description of the Related Art

An aroma delivery device is known which is used in conjunction with a consumable product. A problem with such an aroma delivery device is that it is not a stand-alone device. Further, an air treatment apparatus is known which employs a refill pack containing wax or paraffin granules incorporating a fragrance. A problem with such an air treatment apparatus is that it is not designed as a single-use, disposable apparatus.

Further, it is known to perforate a coffee cup lid with very small through-holes (i.e., five-thousands of an inch) and to use such perforations to tear off, or at least partially remove, a portion of the coffee cup lid relative to a remainder of the lid. Further, it is known to use a packet in the food services industry, the packet including a body, a removable or tear-off covering or lid over the open portion of the body, and a food substance (such as jelly) contained in the body under the covering. It is also known to use a gel-packet in the fragrance industry to contain a fragrance which is emitted from the gel-packet; such gel-packets in the fragrance industry are known to be slid or inserted into a pocket of a housing without using a snap-fit arrangement.

What is needed in the art is an inexpensive, single-use, disposable, stand-alone chemical delivery assembly which uses an exothermic chemical reaction to heat a chemical storage device of the chemical delivery assembly. What is further needed in the art is such a chemical delivery assembly which is simple in design, is easy to assemble, and at least substantially preserves the life of a chemical storage device for the end-user.

SUMMARY OF THE INVENTION

The present invention provides an inexpensive, single-use, disposable, stand-alone chemical delivery assembly which uses an exothermic chemical reaction to heat a chemical storage device of the chemical delivery assembly. The present invention further provides such a chemical delivery assembly which is simple in design, is easy to assemble, and at least substantially preserves the life of a chemical storage device for the end-user.

The invention in one form is directed to a chemical delivery assembly including a heating element which provides an exothermic chemical reaction, a chemical storage device configured for emitting a volatilized chemical therefrom, and a container including a bottom section and a top section, the heating element coupled with the bottom section, the chemical storage device coupled with the top section, the heating element being in thermal communication with the chemical storage device.

The invention in another form is directed to a method of using a chemical delivery assembly, the method including the steps of providing, coupling, heating, communicating, and emitting. The providing step provides a heating element which provides an exothermic chemical reaction, a chemical storage device, and a container including a bottom section and a top section. The coupling step couples the heating element with the bottom section and the chemical storage device with the top section. The heating step heats the heating element. The communicating step thermally communicates the heating element with the chemical storage device. The emitting step emits a volatilized chemical from the chemical storage device.

The invention in yet another form is directed to a chemical delivery system including: a chemical storage device configured for emitting a volatilized chemical therefrom; a heating element which provides an exothermic chemical reaction; an at least substantially rigid housing element containing the heating element; a tray including a well, the well having an absence of a through-hole and defining a space which is slightly larger than the chemical storage device, the tray being attached to the housing element, the chemical storage device being mounted to the well, the heating element being in thermal communication with the chemical storage device via the well; a retainer attached to the well and including at least one hole configured for passing therethrough the volatilized chemical to an ambient environment, the retainer being configured for retaining the chemical storage device in the space; and a removable covering directly attached to the tray and covering the retainer and the well to thereby hermetically seal the chemical storage device within the space.

The invention in yet another form is directed to a chemical delivery system including: a chemical storage device configured for emitting a volatilized chemical therefrom; a heating element which provides an exothermic chemical reaction; an at least substantially rigid exterior housing element including a top portion and containing the heating element; and a lid including a first horizontal wall, a first plurality of vertical walls coupled to one another and depending downwardly from the first horizontal wall, and a well spaced radially inwardly relative to the first plurality of vertical walls and depending downwardly from the first horizontal wall, the chemical storage device being mounted to the well, the heating element being in thermal communication with the chemical storage device via the well, the first plurality of vertical walls being attached to only the top portion of the housing element.

The invention in yet another form is directed to a method of using a chemical delivery system, the method including the steps of: providing a heating element which provides an exothermic chemical reaction, a chemical storage device, and an at least substantially rigid housing element containing the heating element; attaching a tray to the housing element, the tray including a well, the well having an absence of a through-hole and defining a space which is slightly larger than the chemical storage device; mounting the chemical storage device to the well; attaching a retainer to the well, the retainer including at least one hole; retaining, using the retainer, the chemical storage device in the space; removing a removable covering from the tray, prior to the step of removing the removable covering being directly attached to the tray and covering the retainer and the well to thereby hermetically seal the chemical storage device within the space; heating the heating element; thermally communicating the heating element with the chemical storage device via the well; emitting a volatilized chemical from the chemical storage device; and passing the volatilized chemical to an ambient environment through the at least one hole.

An advantage of the present invention is that it is inexpensive.

Another advantage is that it can be a single-use, disposable chemical delivery assembly.

Yet another advantage is that it functions as a stand-alone assembly.

Yet another advantage is that the chemical delivery assembly provides a lid which also functions as a tray for the chemical storage device, the lid being frictionally fit with a housing element.

Yet another advantage is that it can provide a containment area for the chemical storage device that substantially preserves the life of the chemical storage device for the end-user.

Yet another advantage is that it can provide a hermetic seal about the chemical storage device and thereby preserve the life of the chemical storage device for the end-user.

Yet another advantage is that the chemical delivery assembly can be turned on its side or even upside down without the chemical storage device falling out of the lid.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
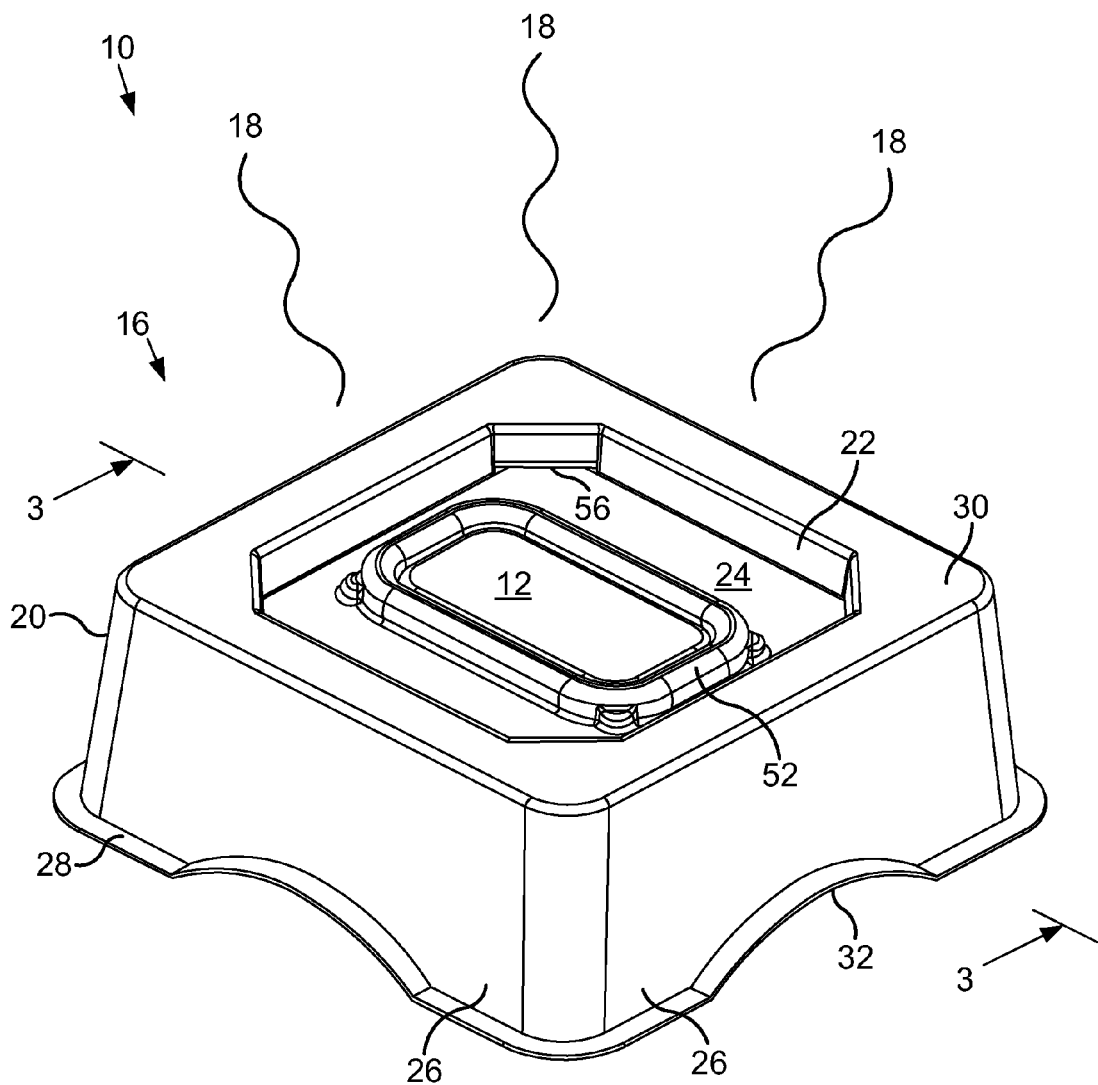
FIG. 1 is a top, perspective view of the chemical delivery assembly according to the present invention.
Figure 2:
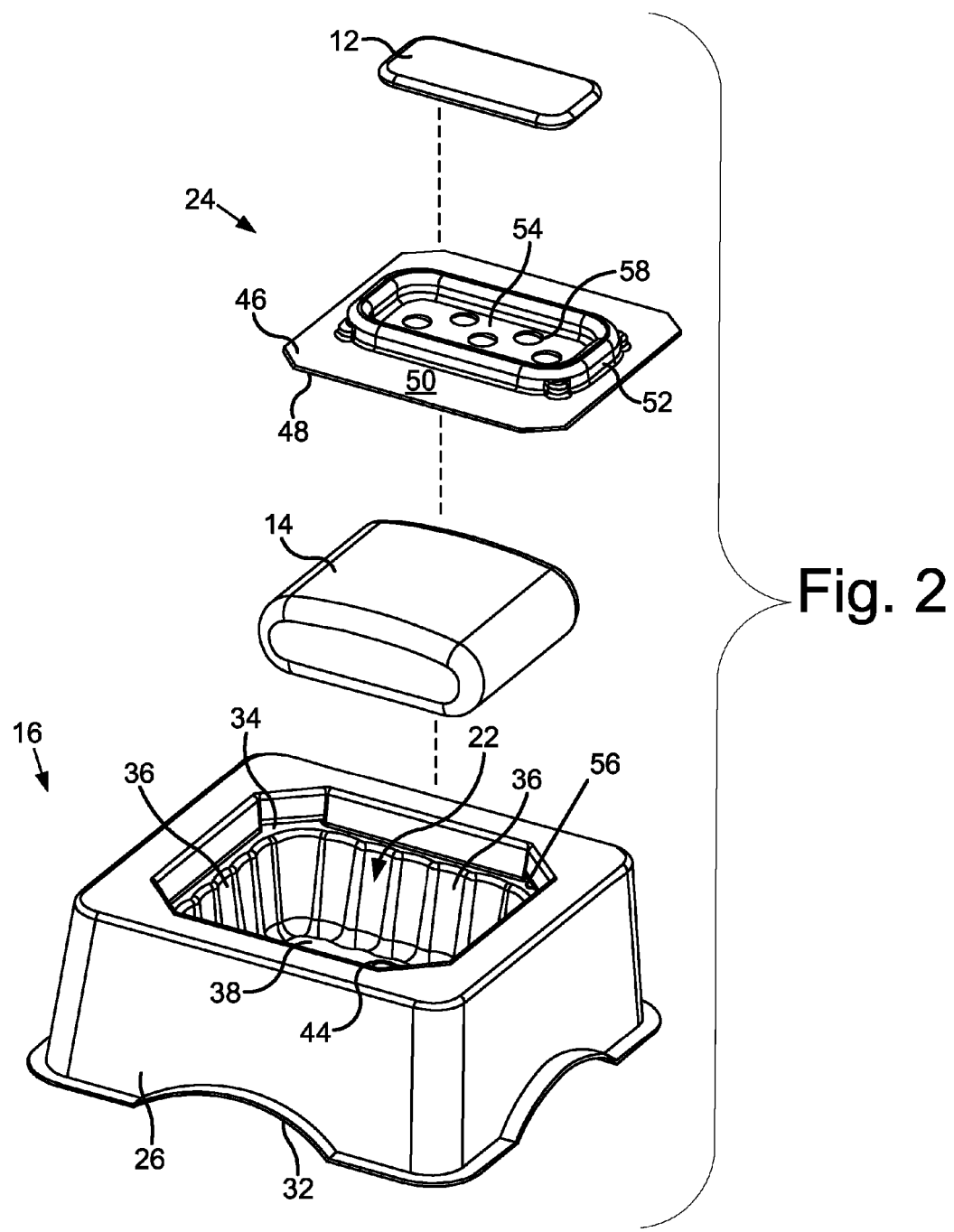
FIG. 2 is an exploded, perspective view of the chemical delivery assembly of FIG. 1.

Referring now to the drawings, and more particularly to FIGS. 1-2, there is shown a chemically delivery assembly 10 which generally includes a chemical storage device 12, a heating element 14, and a container 16. Chemical delivery assembly 10 can be an air freshener/deodorizer assembly, an air cleaner assembly, a bug repellant assembly, an insecticide delivery assembly, and/or generally a vaporizer, for instance, for providing medicinal vapors to the surrounding air. This listing of applications of chemical delivery assembly 10 is not intended to be limiting.

Chemical storage device 12, when heated, emits a volatilized chemical 18. That is, chemical storage device 12, before being heated, includes a chemical that is volatilizable (or, stated another way, can become volatilized). Upon being heated, the chemical volatilizes and is emitted into the surrounding air as volatilized chemical 18. By volatilize, Applicants mean that the chemical can become volatile, can pass off as a vapor. Chemical storage device 12 can include a porous cotton material, for example, which is soaked with a liquid containing volatilizable chemical. Alternatively, chemical storage device can be formed of a plastic fiber material, for example, which holds a liquid, or a gel, containing the volatilizable chemical. Chemical storage device 12 is filled with any suitable air treating material, such as an air deodorizer, an insect repellent, an insecticide, a health care agent, or the like.

Heating element 14 provides an exothermic chemical reaction. This exothermic chemical reaction can be provided in at least one of two ways. The first way provides that heating element 14 is an air-activated oxidation reaction heater. In this instance, heating element 14 can be, for example, an iron oxide heater that, when exposed to air, experiences a chemical reaction which produces heat. That is, heating element 14 undergoes an exothermic chemical reaction and thereby produces heat when heating element 14 is exposed to oxygen from air, the oxygen reacting with one or more chemical constituents of heating element 14. The second way provides that heating element 14 is activated by some other way than simply exposing heating element 14 to air. This could include heating element 14 having chemical constituents that can be caused to react together when, for instance, an end-user bursts a container containing one of these constituents to cause these constituents to come together and react exothermically, or otherwise causes these chemical constituents to come together so as to chemically react. The chemical constituent in the container that bursts can be in the form of water, for example.

Figure 3:
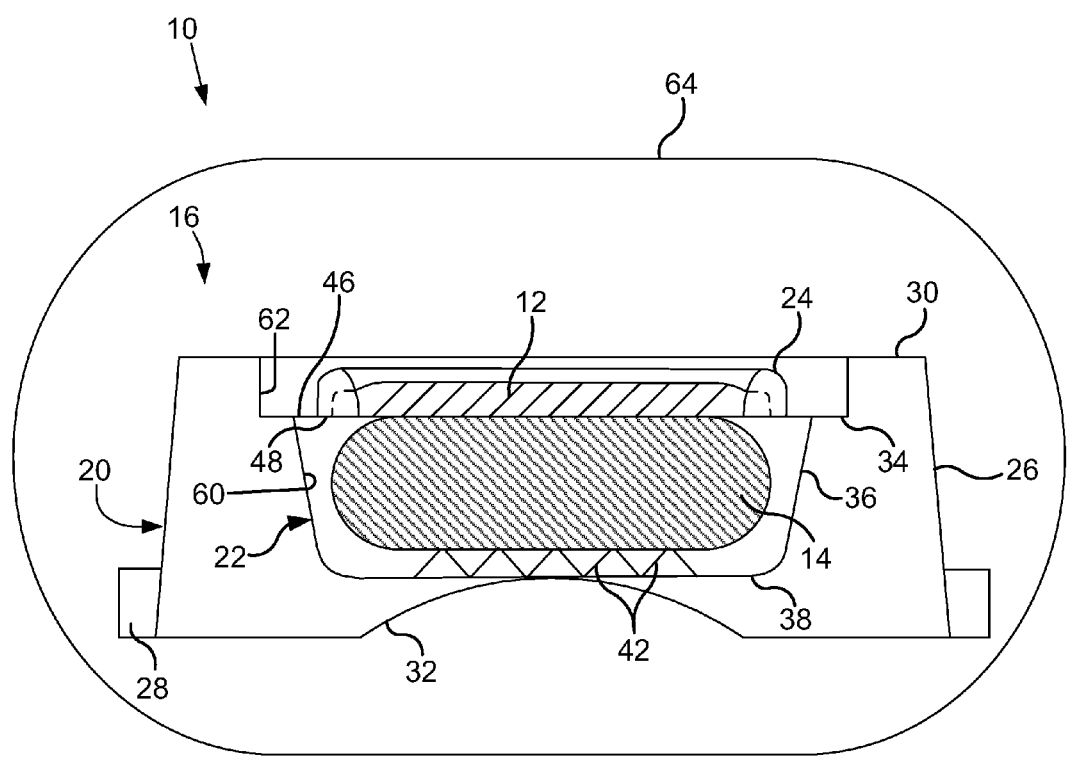
FIG. 3 is a schematic, sectional view of the chemical delivery assembly of FIG. 1 taken along line 3-3.

Container 16 includes a bottom section 60 and a top section 62 (sections 60 and 62 being shown in FIG. 3). Heating element 14 is coupled with bottom section 60, and chemical storage device 12 is coupled with top section 62. Container 16 can be an outer tray 16. Tray 16 includes a body 20, a dividing element 22, and a dividing element 24. Body 20 can be generally square-shaped and include four generally vertical side walls 26 (which can generally slant outwardly running from top to bottom), flanges 28 attached to the bottom of vertical walls 26 (flanges 28 providing a base for tray 16 to contact the surface on which tray 16 rests), and a top wall 30 which is generally parallel to base flanges 28 and to the flat surface (not shown) upon which chemical delivery assembly 10 rests. Side walls 26 serve as legs which support chemical delivery assembly 10 on the surface (not shown) as a stand-alone unit. Further, each of side walls 26 and the corresponding flanges 28 can define an arch 32 (or some differently shaped opening) so as to permit air surrounding the outer portion of tray 16 to easily flow under body 20 and to heating element 14. Body 20 is shaped so that chemical delivery assembly 10 can function as a stand-alone assembly/unit. That is, as a stand-alone assembly/unit, chemical delivery assembly 10 is not connected to another device to perform its function of delivering a volatilized chemical 18 into the surrounding air. Body 20 can be thermoformed plastic (i.e., using pneumatic and/or mechanical pressure forming, or vacuum forming).

Figure 4:
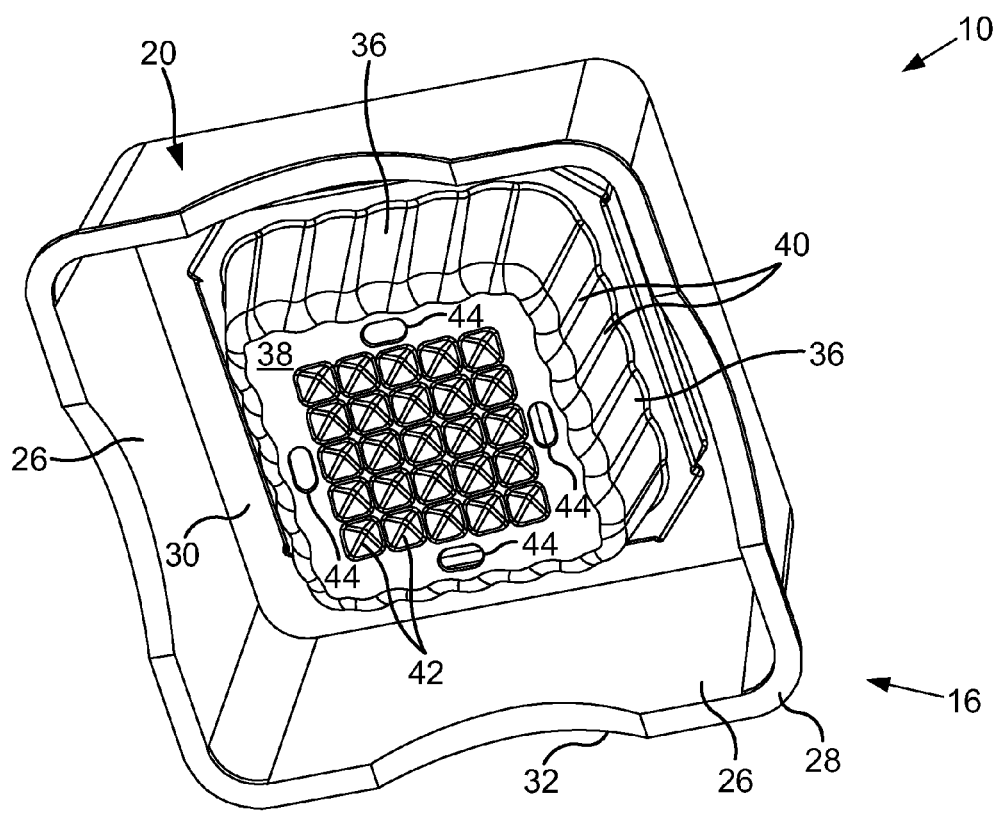
FIG. 4 is a bottom, perspective view of the chemical delivery assembly of FIG. 1.

Dividing element 22 forms a well which has an open surface along top wall 30 of body 20. Dividing element 22 can be made of the same material as body 20, formed at the same time as body 20, and be monolithic with body 20 (dividing element 22 being monolithic with body 20 is shown in the drawings). Dividing element 22 can include four generally vertical side walls 36 depending downwardly from top wall 30 of body 20 (these side walls 36 can decline inwardly running from top to bottom) and a bottom wall 38 connected to the lowest extent of side walls 36. Side walls 36 of dividing element 22 can include ribs 40 which help body 20 from crumbling when body 20 of tray 16 gets hot due to heating element 14. Bottom wall 38 can be formed so as to be positioned above the surface on which chemical delivery assembly 10 is situated given that legs 26 can be longer than side walls 36 of well 24. Bottom wall 38 serves as a mounting platform on which heating element 14 can rest or otherwise be affixed. Bottom wall 38 can include a plurality of raised projections 42 and a plurality of through-holes 44, as shown in FIGS. 3-4. Projections 42 serve to position heating element 14 above the lowest extent of bottom wall 38 such that heating element 14 does not sit flush on the lowest extent of bottom wall 38. Holes 44 permit air to be provided to heating element 14, the air flowing from the space separating side walls 26 and side walls 36 and from outside chemical delivery assembly 10 into that space via arches 32. By raising heating element 14 with projections 42, air is permitted to flow beneath heating element 14 and thereby to come into more surface area contact with the bottom surface of heating element 14 than if heating element 14 sat flush on bottom wall 38 formed as a flat expanse. When air is provided through holes 44 to heating element 14, heating element 14 heats up and thereby heats chemical storage device 12 so that chemical storage device 12 emits volatilized chemical 18.

Dividing element 24 includes two opposing sides 46 and 48. Heating element 14 is mounted on tray 16 to side 46, and chemical storage device 12 is mounted on tray 16 to side 48. In mounting to side 46, heating element 14 may or may not contact side 46. In the embodiment shown in the drawings, chemical storage device 12 is mounted on dividing element 24. Heating element 14 is in thermal communication with chemical storage device 12 via dividing element 24.

Dividing element 24 can be formed as a second tray (i.e., an inner tray 24) which snap-fittingly engages dividing element 22. Dividing element 24 includes a platform 50 (i.e., a wall 50) and a ridge 52 which can be monolithically formed with platform 50. Dividing element 24 forms a tray such that dividing element 24 defines its own well 54 formed by platform 50 and ridge 52. Platform 50 has a generally flat expanse and four corners, although the corners do not necessarily form pointed tips. When dividing element 24 is assembled with outer tray 16, the corners of platform 50 can snap-fit into corresponding slots 56 formed in dividing element 22. Further, these corners, as well as the longitudinal and transverse edges, of platform 50 can rest on a generally horizontal shoulder 34 formed on dividing element 22. Platform 50 can define a plurality of through-holes 58 for directing heat from heating element 14 into chemical storage device 12. Ridge 52 can form an upstanding wall on platform 50, ridge 52 connecting to itself so as to encircle a portion of platform 50; such encircling is meant to include various shapes, such as a circle, an ellipse, a rectangle, and the like. Ridge 52 serves to secure chemical storage device 12 when chemical storage device 12 is mounted on platform 50. Together, the solid portion of platform 50 within well 54 of dividing element 24 and through-holes 58 provide a heat transfer plate which permits the appropriate heat transfer rate from heating element 14 to chemical storage device 12. That is, the solid portion of platform 50 beneath chemical storage device 12 provides for a predetermined rate of heat transfer via conduction, and through-holes 58 beneath chemical storage device 12 provide for a predetermined rate of heat transfer via convection. Rather than having a plurality of through-holes 58, dividing element 24 may have a single hole 58 sized to provide an optimal heat transfer rate from heating element 14 to chemical storage device 12. Dividing element 24 can prevent heating element 14 from being in direct contact with chemical storage device 12, as shown in the drawings. Dividing element 24 can alternatively have a clam-shell design (not shown); that is, dividing element 24 can also include a lid which lies over chemical storage device 12, the lid being similar in appearance to dividing element 24 as shown in the drawings but turned upside down.

Dividing element 24 divides bottom section 60 from top section 62 of container 16. More specifically, side 48 (the bottom side in the drawings) of dividing element 24 divides bottom section 60 from top section 62. Alternatively, one can view shoulder 34 as the dividing line between bottom section 60 and top section 62.

Dividing element 24 can be thermoformed separately from body 20 of tray 16, as chemical storage device 12 and heating element 14 can be formed separately from body 20 of tray 16. Dividing element 24, body 20 and well 22 of tray 16, chemical storage device 12, and heating element 14 can then be assembled with ease in their respective positions during manufacturing to form a single chemical delivery assembly 10. During assembly of chemical delivery assembly 10, heating element 14 can first be placed on projections 42 of bottom wall 38 of well 22. Then, dividing wall 24 can be snap-fittingly engaged with well 22. Then, chemical storage device 12 can be set on, or otherwise mounted to, dividing wall 24. Then, once these parts 12, 14, 16 (which includes dividing elements 22 and 24) are assembled together to form chemical delivery assembly 10, a container 64 can be used to enclose these parts 12, 14, 16 as an assembled group. The container 64 can be used to enclose a vacuum inside such that heating element 14 is in a vacuum and thus not in contact with air before chemical delivery assembly 10 is ready to be used by an end-user. Alternatively, the container 64 can be such that it does not enclose a vacuum therein. In this alternative, a very small amount of air may be enclosed/sealed in the container 64 (so as to avoid having to vacuum seal the container), but this small amount is effectively a negligible amount in the sense that heating element 14 either does not yet begin to heat up or any heating that does occur is very minimal and does not manage to use up heating element 14 before an end-user has the chance to open the container 64 and to use effectively chemical delivery assembly 10. The container 64 is heat-sealed closed so as to enclose chemical delivery assembly 10. The container 64 can be made of a biaxially-oriented polyethylene terephthalate polyester ("boPET") film and can be, for example, MYLAR. The boPET film can be aluminized, which can render the container 64 even less permeable to gasses. As such, the metallized boPET film (which can be referred to as a "foil") can protect the contents of the container 64 against oxidation. Alternatively, dividing element 24 can be formed monolithically with body 20 of tray 16.

Chemical delivery assembly 10 can be a single-use, disposable assembly. That is, chemical delivery assembly 10 is manufactured inexpensively and designed to be discarded when it no longer emits volatilized chemical 18. Chemical delivery assembly 10 no longer emits volatilized chemical 18 when heating element 14 ceases to produce heat and/or chemical storage device 12 no longer contains the volatilizable chemical. Further, chemical delivery assembly 10 can have a relatively short life span. That is, chemical delivery assembly 10 may cease to function (as described above) after about forty-eight hours. Chemical delivery assembly 10 may not be designed such that an end-user can replace heating element 14 and/or replace or refill chemical storage device 12.

In use, chemical delivery assembly 10 is removed from the container 64 and placed on a surface (i.e., a floor of a room). Upon doing so, an abundance of air is provided to heating element 14 via holes 44. Upon being provided with a sufficient amount of air, heating element 14 produces an exothermic chemical reaction which eventually heats chemical storage device 12. Upon being heated (or at least to a certain, predetermined degree), chemical storage device 12 emits volatilized chemical 18 into the air surrounding chemical delivery assembly 10. When heating element 14 stops producing heat or when chemical storage device 12 has exhausted its supply of the volatilizable chemical, chemical delivery assembly 10 is discarded. Alternatively, if chemical delivery assembly is designed such that heating element 14 is activated using another way besides air-activation (as described above), chemical delivery assembly 10 can be designed so that heating element 14 is accessible to an end-user in order to activate heating element 14 or is accessible using water, for example.

The present invention also provides a method of using chemical delivery assembly 10. The method includes the steps of providing, coupling, heating, communicating, and emitting. The providing step provides heating element 14 which provides an exothermic chemical reaction, chemical storage device 12, and container 16 including bottom section 60 and top section 62. The coupling step couples heating element 14 with bottom section 60 and chemical storage device 12 with top section 62. The heating step heats heating element 14. The communicating step thermally communicates heating element 14 with chemical storage device 12. The emitting step emits volatilized chemical 18 from chemical storage device 12. Chemical delivery assembly can be a single-use, disposable assembly. Container 16 can be a first tray 16 which includes dividing element 24 which divides top section 62 from bottom section 60, chemical storage device 12 being mounted on dividing element 24, heating element 14 being in thermal communication with chemical storage device 12 via said dividing element 24. Tray 16 can include dividing element 22, dividing element 24 including a second tray 24 and being snap-fittingly engaged with dividing element 22. The method can further include directing heat into chemical storage device 12 using holes 58 defined by wall 50 of tray 24. The method can further include mounting heating element 14 to dividing element 22 of said tray 16 and providing air to heating element 14 using holes 44 defined by dividing element 22. When air is provided to heating element 14, heating element 14 heats up and thereby heats chemical storage device 12 so that chemical storage device 12 emits volatilized chemical 18. Tray 16 includes body 20 which supports chemical delivery assembly 10 as a stand-alone unit, body 20 being monolithic with dividing element 22.

Figure 5:
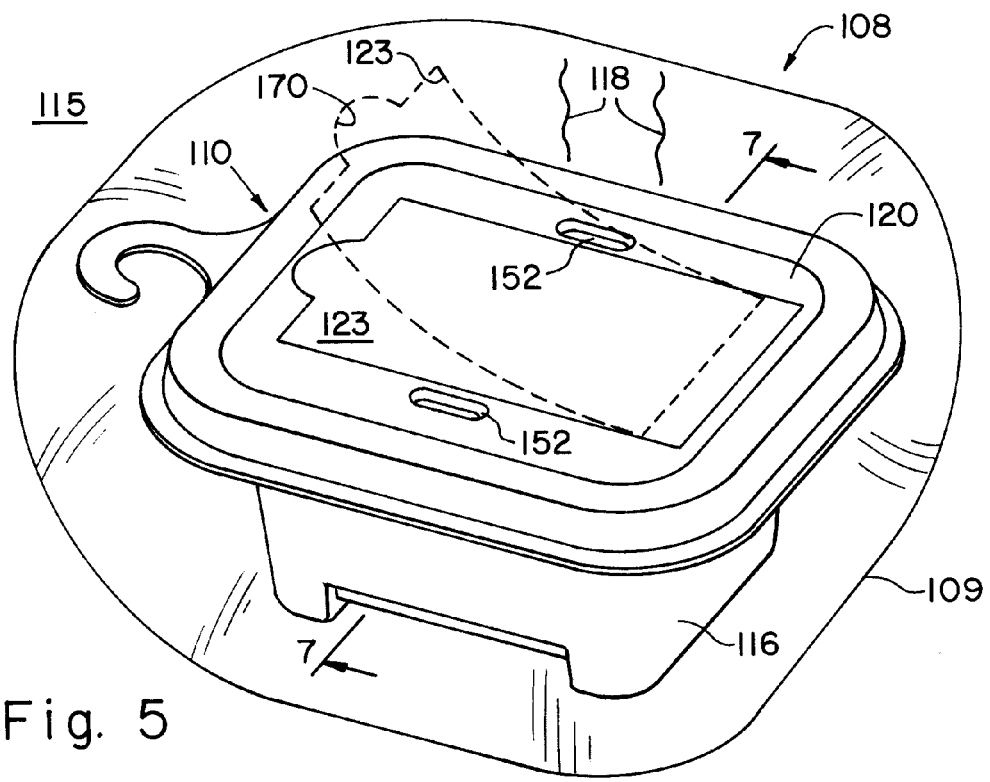
FIG. 5 is a perspective view of another embodiment of the chemical delivery system according to the present invention, the chemical delivery system including a chemical delivery assembly.
Figure 7:
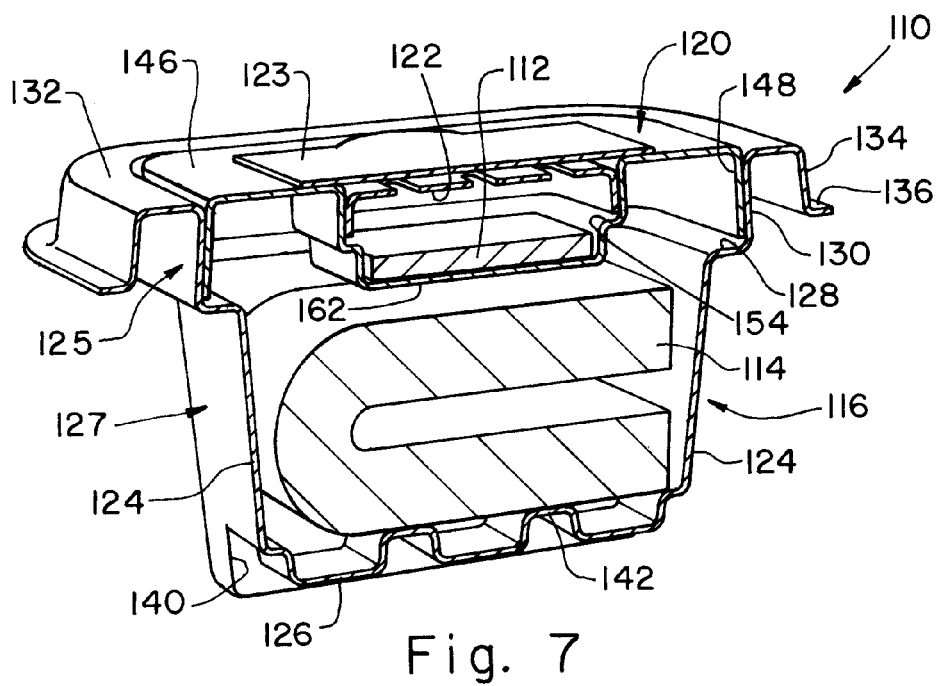
FIG. 7 is a sectional view of the chemical delivery assembly of FIG. 5 taken along line 7-7.
Figure 6:
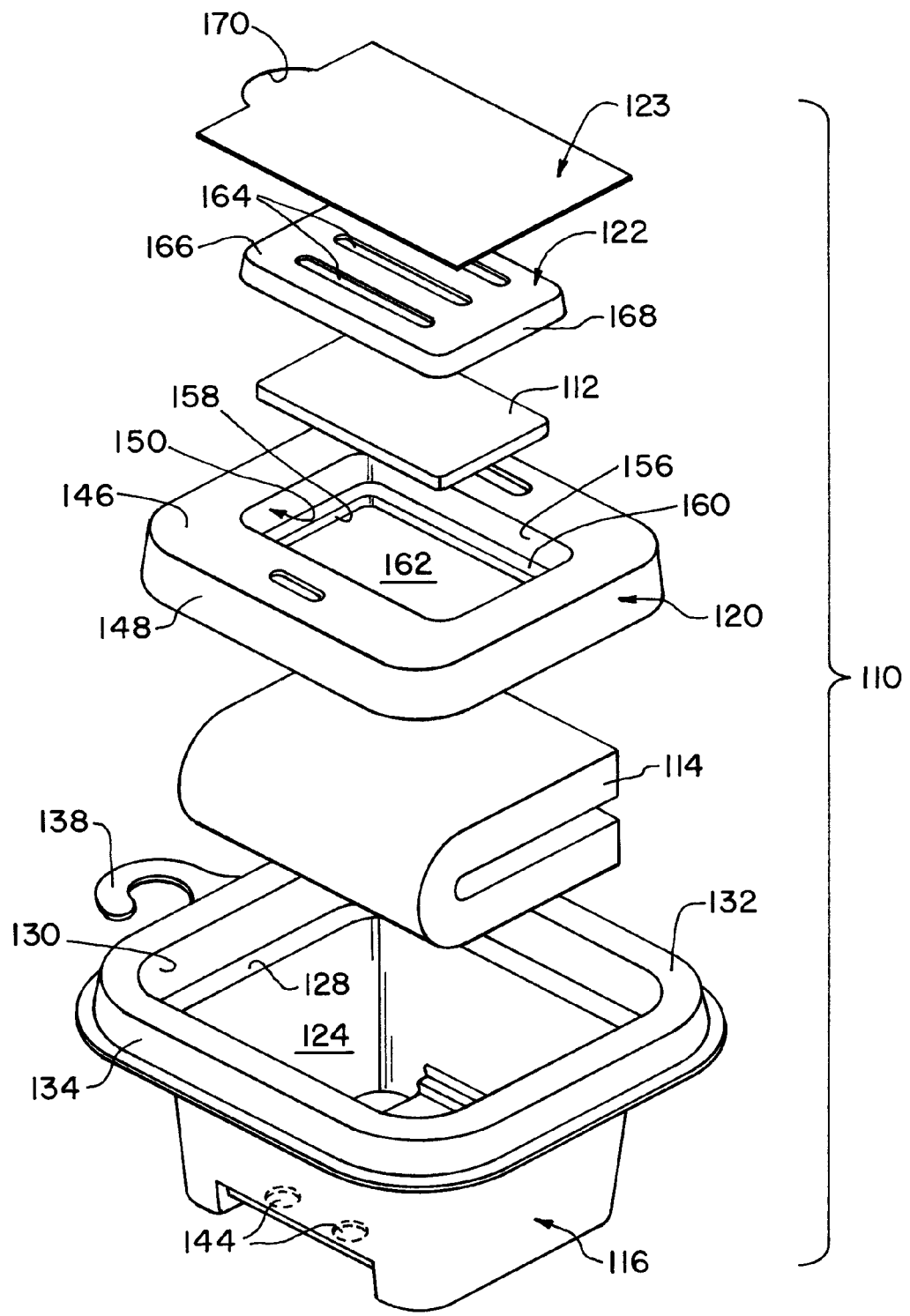
FIG. 6 is an exploded, perspective view of the chemical delivery assembly of FIG. 5.

Referring now to FIGS. 5-7, FIGS. 5-7 show an embodiment of the chemical delivery system 108 of the present invention. Chemical delivery system 108 generally includes a chemical delivery assembly 110 and an enclosure 109 which surrounds and encloses chemical delivery assembly 110. Chemical delivery assembly 110 generally includes a chemical storage device 112, a heating element 114, a housing element 116, a tray 120, a retainer 122, and a covering 123. Chemical delivery assembly 110 can be a scent generator and/or dispenser, a disposable heated lure dispenser (for example, a deer lure using urine), an air freshener/deodorizer assembly, an air cleaner assembly, a bug repellant assembly, a fragrance generator and/or dispenser, an insecticide delivery assembly, and/or generally a vaporizer, for instance, for providing medicinal vapors to the surrounding air. This listing of applications of chemical delivery assembly 110 is not intended to be mutually exclusive and is provided merely by way of example and is not intended to be limiting.

Chemical storage device 112 is configured for emitting a volatilized chemical 118 therefrom. Chemical storage device 112 can be at least substantially identical to chemical storage device 12 and thus function in at least a substantially similar manner. Chemical storage device 112, optionally, can be a pad (for example, a cotton pad) that is filled with natural or synthetic deer urine so that chemical delivery assembly 110 can function as a deer lure. The volatilizable chemical does not volatilize to the ambient environment 115 volatilized chemical 118 until covering 123 is peeled back from tray 120.

Heating element 114 provides an exothermic chemical reaction. Heating element 114 can be at least substantially identical to heating element 14 and thus function in at least a substantially similar manner. FIGS. 6 and 7 show heating element 114 in a folded condition.

Housing element 116 is at least substantially rigid and serves as the exterior of chemical delivery assembly 110. As a substantially rigid exterior housing element, housing element 116 can have some elasticity (such as a thermoplastic device) which enables chemical delivery assembly 110 to be a stand-alone device on a horizontal surface, for example. Housing element includes a top portion and a bottom portion 127. Top portion 125 is attached to tray 120. Housing element 116 contains heating element 114 at least substantially in bottom portion 127. Housing element 116 defines a space below tray 120 in which heating element 114 is placed. Housing element 116 includes four vertical side walls 124 coupled to one another (which can generally slant outwardly running from the bottom), a bottom wall 126 formed near the bottom of housing element 116 and attached to the bottom of side walls 124, a horizontal shoulder 128 attached to the top of side walls 124 and running radially outwardly therefrom, four vertical walls 130 coupled to another another and attached to the radial outer perimeter of horizontal shoulder 128 and running upwardly (at least generally vertically) therefrom, a horizontal top wall 132 attached to the top of vertical walls 130 and running radially outwardly therefrom, four vertical walls 134 coupled to one another and attached to the radial outer perimeter of horizontal top wall 132 and running downwardly therefrom, a horizontal flange 136 attached to the bottom of vertical walls 134 and running radially outwardly therefrom, and a hanger or hook extending outwardly from flange 136. As with the other plurality of vertical walls described herein (i.e., 130, 134, 148, 156, 158, 168), for simplicity in the drawings less than all of the vertical walls 124 are labeled in the drawings. It is understood, for example, that the other vertical walls which are coupled with (and thus form an enclosed perimeter with) the at least one vertical wall 124 that is labeled and that are similar to the at least one vertical wall 124 which is labled are also vertical walls 124; the same applies to the other plurality of vertical walls. Top portion 125 includes horizontal shoulder 128, vertical walls 130, horizontal top wall 132, vertical walls 134, flange 136, and hanger 138. Bottom portion 127 includes side walls 124 and bottom wall 126. Side walls 124 serve as legs which support chemical delivery assembly 110 on a surface (not shown) as a stand-alone unit. Further, at least one side wall 124 can define an arch 140 (or some differently shaped opening 140) so as to permit air surrounding the outer portion of housing element 116 to easily flow under housing element 116 and to heating element 114. FIGS. 5-7 show such an opening 140 in side wall 124. According to one embodiment, two opposing side walls 124 define such an opening 140. Bottom wall 126 of housing element 116 serves as a mounting platform on which heating element 114 can rest or otherwise be affixed. Bottom wall 126 can include a plurality of ribs 142 and a plurality of holes 144. Ribs 142 serve to position heating element 114 above the lowest extent of bottom wall 126. Although not shown in the drawings, according to one embodiment of the present invention bottom wall 126 can include six holes 144 in the troughs between ribs 142, two holes spaced apart along the length of each of the troughs shown in FIG. 7; less or more holes 144 can be used. Two holes 144 are shown schematically in broken lines in FIG. 6 merely for general illustrative purposes. Holes 144 in the bottom wall 126 permit air to be provided to heating element 114; the air flows from outside chemical delivery assembly 110, through arches/openings 140, and through holes 144 in bottom wall 126. When air is provided through holes 126 to heating element 114, heating element 114 heats up and thereby heats chemical storage device 112 so that chemical storage device 112 emits the volatilized chemical 118. Housing element 116 is shaped so that chemical delivery assembly 110 can function as a stand-alone assembly/unit. Housing element 116 can be thermoformed plastic (i.e., using pneumatic and/or mechanical pressure forming, or vacuum forming). Hanger 138 is formed as a hook and can be used to hang chemical delivery assembly 110 (i.e., from a tree limb).

Tray 120 can also be referred to as lid 120, as tray 120 serves as a lid for housing element 116. Tray 120 is attached to housing element 116, chemical storage device 112 being mounted to tray 120 (FIG. 7 shows that chemical storage device 112 is mounted on tray 120), heating element 114 being in thermal communication with chemical storage device 112 via tray 120. Tray 120 includes a first horizontal wall 146, a first plurality of vertical walls 148, and a well 150. First horizontal wall 146 of tray 120 can be referred to as top horizontal wall 146. At the outer radial extent of first horizontal wall 146 are vertical walls 148, and at the inner radial extent of first horizontal wall 146 is well 150. First horizontal wall 146 can define through-holes 152 (for example, two such through-holes 152) which help equalize the pressure within the space of housing element 114 below tray 120, particularly when heating element 114 is activated. Vertical walls 148 are positioned at the outer perimeter of tray 120. Vertical walls 148 are coupled to one another and depend downwardly from horizontal wall 146. Vertical walls 148 are attached to housing element 116. Vertical walls 148 are attached to only top portion 125 of housing element 116. Vertical walls 148 of tray 120 can form an interference fit with vertical walls 130 of housing element 116 and/or be bonded (i.e., using an adhesive) thereto. Vertical walls 148 of tray 120 fit radially within vertical walls 130 of housing element 116.

Well 150 has an absence of a through-hole and defines a space 154 which is slightly larger than chemical storage device 112, chemical storage device 112 being mounted to well 150, heating element 114 being in thermal communication with chemical storage device 112 via well 150. Well 150 is spaced apart from vertical walls 148. More specifically, well 150 is spaced radially inwardly relative to vertical walls 148 and depend downwardly from first horizontal wall 146. Well 150 includes a second plurality of vertical walls 156, a third plurality of vertical walls 158, a horizontal shoulder 160, and a second horizontal wall 162. Vertical walls 156 are coupled to one another, are spaced radially inwardly relative to vertical walls 148, and depend downwardly from first horizontal wall 146. Vertical walls 158 are coupled to one another and are spaced radially inwardly relative to vertical walls 156. Horizontal shoulder 160 couples vertical walls 156 with vertical walls 158. A radial outer extent of horizontal shoulder 160 is attached to the bottom of vertical walls 156, horizontal shoulder 160 running radially inwardly from the bottom of vertical walls 156. A radial inner extent of horizontal shoulder 160 is attached to the top of vertical walls 158 such that vertical walls 158 depend from shoulder 160, horizontal shoulder 160 running radially outwardly from the top of vertical walls 158. Second horizontal wall 162 is connected to vertical walls 158. Second horizontal wall 162 is a bottom wall of well 150 and is formed as a flat expanse or platform which is attached to the bottom of vertical walls 158. Second horizontal wall 162 includes no holes formed therein and is thus a solid wall. Chemical storage device 112 is mounted on second horizontal wall 162 and thereby is received in well 150 and sits on second horizontal wall 162; Chemical storage device 112 may not be otherwise affixed to well 150. Second horizontal wall 162 of tray 120 serves as a heat transfer plate which permits the appropriate heat transfer rate from heating element 114 to chemical storage device 112. That is, second horizontal wall 162 beneath chemical storage device 112 provides for a predetermined rate of heat transfer via conduction.

Retainer 122 (which can also be referred to as a lid 122) is attached to well 150 and includes at least one hole 164 configured for passing therethrough the volatilized chemical 118 to the ambient environment (the environment surrounding chemical delivery assembly 110). Retainer 122 is configured for retaining chemical storage device 112 in the space 154 defined by well 150. Retainer 122 includes a third horizontal wall 166 and a fourth plurality of vertical walls 168. Third horizontal wall 166 is formed as a flat expanse which includes at least one through-hole 164 which is configured for passing therethrough the volatilized chemical 118 to the ambient environment; FIGS. 6 and 7 show third horizontal wall 166 including three slots 164. Vertical walls 168 are coupled to one another and depend downwardly from third horizontal wall 166. Retainer 122 can be frictionally attached to tray 120 using an interference fit; more specifically, vertical walls 168 can form an interference fit with vertical walls 156 of tray 120. Alternatively or in addition thereto, vertical walls 168 can be bonded (for example, using an adhesive) with vertical walls 156 of tray 120. Vertical walls 168 are prevented from descending further downwardly into well 150 by horizontal shoulder 160.

Covering 123 is directly attached to tray 120. More specifically, covering 123 is directly attached to the outer surface of horizontal wall 146 of tray 120 (which can be referred to as lid 120, as indicated above). Covering 123 can be bonded to tray 120 using, for example, an adhesive. Covering 123 covers retainer 122 (in particular, through-holes 164 formed in retainer 122) and well 150 to thereby hermetically seal chemical storage device 112 within the space 154 defined by well 150 (as a hermetic seal, covering 123 prevents additional air from entering space 154 and prevents air already in space 154 from leaving space 154). Covering 123 is removable and thus during normal use is removed (for example, torn off by the end-user) from horizontal wall 146 to expose chemical storage device 112 underneath to ambient air and to permit volatilized chemical 118 to be emitted into the ambient air surrounding chemical delivery assembly 112. FIG. 5 shows covering 123 in solid lines attached to tray 120 and also in broken lines after being partially torn away from tray 120. Covering 123 thus functions as a seal until it is removed. Covering 123 can be a foil and thus be referred to as a foil seal. As a removable covering 123, covering 123 is a peelable foil seal. Covering 123 can include a tab 170 which is not bonded to tray 120 or retainer 122, tab 170 being configured for being grasped by an end-user and thereby for being pulled or otherwise torn off of tray 120 (and thus also taken off of retainer 122) to expose retainer holes 164, and thus also chemical storage device 112, to the ambient environment. As indicated above, chemical storage device 112 can be a pad containing natural or synthetic deer urine that emits scent molecules into the air when heated (this application of the chemical storage device is provided by way of example and is not intended to be limiting, as the chemical delivery assembly could be used, merely by way of example, to generate and/or dispense other kinds of scents or chemicals, as disclosed above). If such a pad 112 is not sealed off during nonuse of chemical delivery assembly 110, the deer urine on the pad 112 will evaporate from the pad 112 and the pad 112 would thus lose its value for the end-user. A sealed-off area for chemical storage device 112 is thus formed by the solid portion of tray 120 (that portion of tray 120 lacking through-holes) and tear-off covering 123. If through-holes were formed in second horizontal wall 156 of well 150 or if covering 123 were omitted from covering holes 164 of retainer 122, then the deer urine would evaporate from chemical storage device 112 even while chemical delivery assembly 110 is stored in an enclosure 109 (i.e., a bag around chemical delivery assembly 110) or would at least evaporate (be used-up) too soon after unsealing enclosure 109. Thus, the lack of holes in well 150 around chemical storage device 112 and covering together form a sealed area around chemical storage device 112 to prevent evaporation of the volatilizable chemical from chemical storage device 112 while chemical delivery assembly 110 is in enclosure 109 until enclosure 109 is opened and covering 123 is removed.

Housing element 116, tray 120, and retainer 122 can be thermoformed (i.e., using a molding operation) separately from one another and then assembled together, as indicated above. Upon assembly chemical delivery assembly 110 together, chemical delivery assembly 110 can be enclosed in enclosure 109 (i.e., a plastic bag).

Chemical delivery assembly 110 can be a single-use, disposable assembly. That is, chemical delivery assembly 110 is manufactured inexpensively and designed to be discarded when it no longer emits the volatilized chemical 118. Chemical delivery assembly 110 no longer emits the volatilized chemical 118 when heating element 114 ceases to produce heat and/or chemical storage device 112 no longer contains the volatilizable chemical. Further, chemical delivery assembly 110 can have a relatively short life span. That is, chemical delivery assembly 110 formed as a deer lure may cease to function (as described above) after about four hours (this application of chemical delivery assembly 110 is provided by way of example and is not intended to be limiting, as disclosed above).

Enclosure 109 surrounds and encloses chemical delivery assembly 110. A bag can be used as enclosure 109. Chemical delivery assembly 110 is removed from enclosure 109 by end-user when end-user is ready to use chemical delivery assembly 110. According to one alternative, enclosure 109 is vacuum-sealed. That is, enclosure 109 can be used to enclose a vacuum therein so that heating element 114 is in a vacuum and thus is not in contact with air before chemical delivery assembly 110 is ready to be used by end-user. Alternatively, enclosure 109 can be such that it does not enclose a vacuum therein. In this alternative, enclosure 109 can be heat-sealed (or otherwise sealed to form an air-tight enclosure) and a small amount of air may be enclosed/sealed in enclosure 109 (so as to avoid having to vacuum seal enclosure 109). Because of the presence of this small amount of air in enclosure 109, heating element 114 activates (as an air-activated heating element 114) for a short time, uses up the oxygen sealed inside enclosure 109, and then deactivates (because oxygen is no longer present) until enclosure 109 is opened later by end-user (the amount of oxygen present in enclosure 109 upon sealing enclosure 109 is not enough to use up heating element 114); heating element 114 then reactivates (starts heating again) when enclosure 109 is opened by end-user. Enclosure 109 can be heat-sealed closed so as to enclose chemical delivery assembly 110 therein. Enclosure 109 can be a plastic bag. Alternatively, enclosure 109 can be made of a biaxially-oriented polyethylene terephthalate polyester ("boPET") film and can be, for example, MYLAR. The boPET film can be aluminized, which can render enclosure 109 even less permeable to gasses. As such, the metallized boPET film (which can be referred to as a "foil") can protect the contents of enclosure 109 against oxidation.

During assembly of chemical delivery system, heating element 114 is placed onto bottom wall 126 of housing element 116; heating element 114 need not be otherwise affixed to bottom wall 126. Heating element 114 may first be folded so as to fit within the space provided for heating element 116 in housing element 114. Tray 120 is then connected to housing element 116. More specifically, vertical walls 148 of tray 120 form an interference fit with vertical walls 130 of housing element 116. Then, chemical storage device 112 is placed onto second horizontal wall 156 of well 150 of tray 120. Retainer 122 is then attached to well 150 of tray 120; more specifically, vertical walls 168 of retainer 122 form an interference fit with vertical walls 158 of well 150 and can be stopped by horizontal shoulder 160 of well 150. Covering 123 can then be secured to first horizontal wall 146 of tray 120 by, for example, an adhesive. Holes 152 formed in first horizontal wall 146 of tray 120 may not be covered by covering 123; in this way, heating element 114 can actuate for a short period of time after chemical delivery assembly 110 is sealed in enclosure 109 so that heating element 114 uses up the oxygen in enclosure 109 to thereby form a vacuum in enclosure 109 without having to vacuum seal enclosure 109. Optionally, tray 120 may be connected to chemical storage device 112, retainer 122, and covering 123 prior to tray 120 being attached to housing element 116. After assembling chemical delivery assembly 110, chemical delivery assembly 110 is enclosed by enclosure 109, as described above.

In use, chemical delivery assembly 110 is removed from enclosure 109 and placed on a surface or hung using hanger/hook 138 of housing element 116. Further, covering 123 is removed from tray 120. Upon removing chemical delivery assembly 110 from enclosure 109, an abundance of air is provided to heating element 114 via holes 144 through bottom wall 126 of housing element 116; stated another way, holes 144 in bottom wall 126 of housing element 116 allow an in-rush of air into housing element 116 so as to activate heating element 114. Upon being provided with a sufficient amount of air, heating element 114 produces an exothermic chemical reaction which eventually heats chemical storage device 112 via tray 120. Upon being heated, chemical storage device 110 emits the volatilized chemical 118 into the air surrounding chemical delivery assembly 110 via holes 164 in retainer 122. When heating element 114 stops producing heat or when chemical storage device 112 has exhausted its supply of the volatilizable chemical, chemical delivery assembly 110 can be discarded.

According to one embodiment of chemical delivery assembly 110, chemical delivery assembly 110 is a disposable heated lure dispenser, in particular a heated buck lure dispenser (i.e., a doe-in-rut buck lure) which can be placed on the ground or hung on a tree limb (this application of chemical delivery assembly 110 is provided by way of example and is not intended to be limiting, as disclosed above). Chemical storage device 112 (i.e., the scent pad) can come pre-loaded with a proprietary formula that is or contains the volatilizable chemical. Chemical storage device 112 can be permeated with this formula which can simulate a doe in her estrus period. Chemical storage device 112 can include urine collected from live whitetail doe in their estrous cycle. The chemical stored by chemical storage device 112 can be 100% natural deer urine (i.e., doe urine to lure a buck). The heating element 114 can be air-activated and provide natural heat. The buck lure (chemical storage device 112) can be effective in cold and freezing weather and last approximately four hours. The heated lure (chemical storage device 112) can put scent molecules into the air. Chemical delivery assembly 110 can be used during pre-rut and rut seasons when bucks are looking for a doe to breed. Once a hunter reaches his/her stand location, the hunter can open the wrapper (enclosure 109) containing chemical delivery assembly 110. Chemical delivery assembly 110 is removed from enclosure 109 and heating element 114 (which is air-activated) instantly begins to warm chemical storage device 112. Chemical delivery assembly 110 can be placed up-wind of a deer trail. To increase the lure strength, the hunter can add 10 to 15 drops of the proprietary formula to the chemical storage device 112 into slots 164 of retainer 122. It may be advisable not to use chemical delivery assembly 110 in oxygen-rich environments, not to open heating element 114, not to allow contents of heating element 114 or chemical storage device 112 to come into contact with eyes or mouth. Heating element 114 can contain iron powder, water, salt, activated charcoal, and vermiculite. Once covering 123 is removed from tray 120 or sufficiently peeled back on tray 120 to expose holes 164 to ambient air, chemical storage device 112 can begin to emit the volatilized chemical 118 therefrom. Housing element 116, tray 120, and retainer 122 can be thermoformed and made of a thermoplastic or thermoset material.

The present invention further provides a method of using chemical delivery system 108. The method includes: providing heating element 114 which provides an exothermic chemical reaction, chemical storage device 112, and an at least substantially rigid housing element 116 containing heating element 114; attaching tray 120 (also known as lid 120) to housing element 116, tray 120 including well 150, well 150 having an absence of a through-hole and defining space 154 which is slightly larger than chemical storage device 112; mounting chemical storage device 112 to well 150; attaching retainer 122 to well 150, retainer 122 including at least one hole 164; retaining, using retainer 122, chemical storage device 112 in space 154; removing removable covering 123 from tray 120, prior to the step of removing removable covering 123 being directly attached to tray 120 and covering retainer 122 and well 150 to thereby hermetically seal chemical storage device 112 within space 154; heating heating element 114; thermally communicating heating element 114 with chemical storage device 112 via well 150; emitting a volatilized chemical 118 from chemical storage device 112; and passing volatilized chemical 118 to an ambient environment 115 through at least one hole 164. Retainer 122 can be frictionally attached to tray 120. Tray 120 includes first horizontal wall 146 and first plurality of vertical walls 148 coupled to one another and depending downwardly from first horizontal wall 146, first plurality of vertical walls 148 being attached to housing element 116, well 150 being spaced apart from first plurality of vertical walls 148 and depending downwardly from first horizontal wall 146. Well 150 includes second plurality of vertical walls 156 coupled to one another and spaced radially inwardly relative to first plurality of vertical walls 148 and depending downwardly from first horizontal wall 146, third plurality of vertical walls 158 coupled to one another and spaced radially inwardly relative to second plurality of vertical walls 156, horizontal shoulder 160 coupling second plurality of vertical walls 156 with third plurality of vertical walls 158, and second horizontal wall 162 connected to third plurality of vertical walls 158, chemical storage device 112 being mounted on second horizontal wall 162. Retainer 122 includes third horizontal wall 166 and fourth plurality of vertical walls 168 coupled to one another and depending downwardly from third horizontal wall 166, fourth plurality of vertical walls 168 forming an interference fit with second plurality of vertical walls 156, third horizontal wall 166 including at least one hole 164. Covering 123 can be a peelable foil seal.

Figure 8:
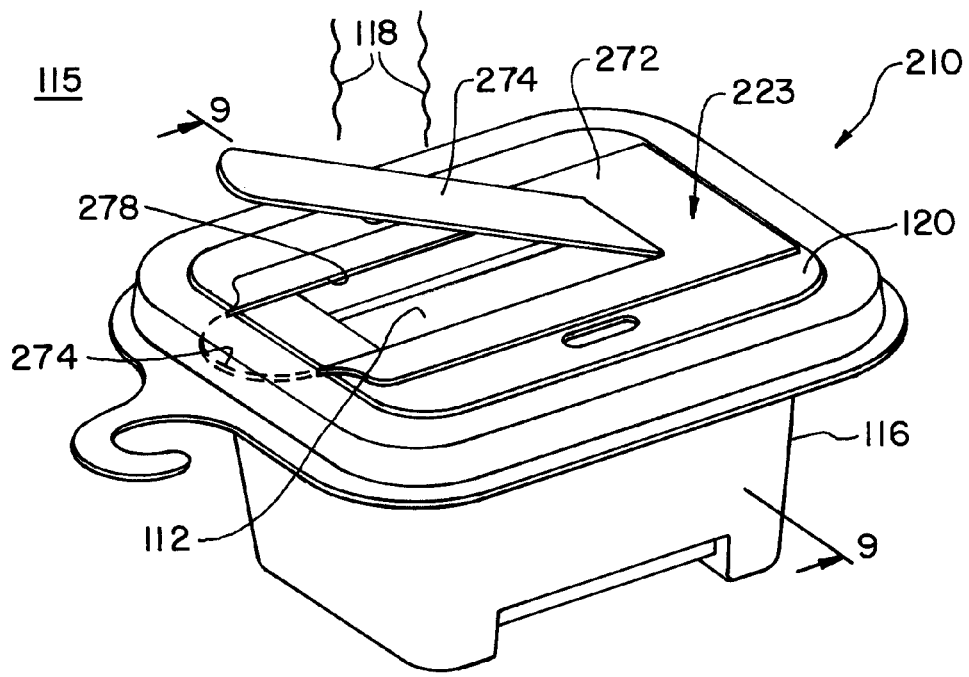
FIG. 8 is a perspective view of yet another embodiment of the chemical delivery assembly according to the present invention.
Figure 9:
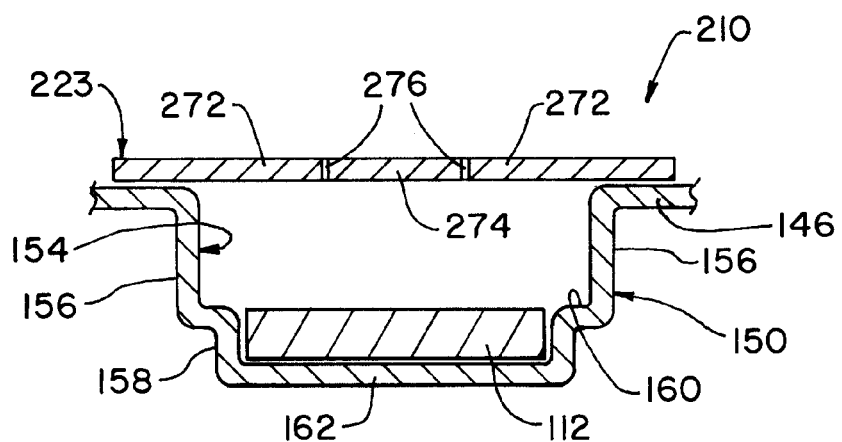
FIG. 9 is a sectional view of part of the chemical delivery assembly of FIG. 8 taken along line 9-9.

Now, additionally referring to FIGS. 8 and 9, there is shown another embodiment of the chemical delivery assembly of the present invention, that assembly having the reference number 210. Like chemical delivery assembly 110, chemical delivery assembly 210 is used in conjunction with an enclosure 109 (i.e., a bag), chemical delivery assembly 210 and enclosure 109 being parts of a chemical delivery system; enclosure 109 is thus not shown in FIGS. 8-9. Chemical delivery assembly 210 is the same as chemical delivery assembly 110 in all respects except that chemical delivery assembly does not include retainer 122 or covering 123; thus, many of the structural components of chemical delivery assembly 210 have the same reference characters as those of chemical delivery assembly 110. While the well of chemical delivery assembly 210 is shown in FIG. 9 as being the same as well 150 (and thus receiving the reference character 150 as well), the well of chemical delivery assembly 210, in an alternative embodiment of the present invention, can omit the stepped construction of well 150; that is, the well of chemical delivery assembly 210 could simply be substantially a rectangular box with an open top. While chemical delivery assembly 210 omits covering 123, chemical delivery assembly 210 includes a covering 223 instead.

Covering 223 covers well 150 to thereby substantially seal chemical storage device 112 within space 154. Covering 223 includes a first part 272, a second part 274, and a plurality of holes 276 at least partly defining first part 272 relative to second part 274. First part 272 is directly attached to first horizontal wall 146 of lid 120, as shown in FIG. 9 and also in broken lines in FIG. 8. Second part 274 is configured for being at least partly removed relative to first part 272 along holes 276 to thereby form an opening 278 for passing therethrough volatilized chemical 118 to ambient environment 115. FIG. 8 shows in solid lines second part 274 partially removed or torn away from first part 272 and in broken lines not yet even partially removed from first part 272. FIG. 9 shows second part 274 in the down position and not yet even partially removed from first part 272. Opening 278 is smaller than chemical storage device 112 and thereby is configured for preventing chemical storage device 112 from exiting well 150. Specifically, FIG. 9 shows that the distance between the lateral edges of chemical storage device 112 is greater than the distance between holes 276, the tearing of second part 274 along holes 276 defining, at least in part, opening 278. Holes 276 are through-holes through the thickness of covering 223, as shown in FIG. 9. Each of holes 276 can be five-thousandths of an inch in diameter and thus according to such an embodiment would be very small (holes 276 in FIG. 9 are not shown to scale). In this way, while some leakage of moisture and/or of the volatilizible chemical from chemical storage device 112 may occur through holes 276, the amount of such leakage would be very small and thus tolerable such that chemical storage device 112 would still have a useful life to the end-user upon removing chemical delivery assembly 210 from the enclosure. Thus, covering 223 substantially seals chemical storage device 112 within space 154 and thus within well 150 in the sense that chemical storage device 112 remains useful for a desired amount of time by the end-user; thus, for all practical purposes, covering 223 forms a substantial hermetic seal of chemical storage device 112 within space 154. Holes 276 are shown in FIG. 9 separating first part 272 from second part 274. It is understood that the parallel lines in FIG. 8 forming the separation between first part 272 and second part 274 include a plurality of holes 276 formed thereon to facilitate the tearing of second part 274 relative to first part 272. The fold or bend line in FIG. 8 extending between the two parallel lines may not also include such holes 276; in this embodiment, second part 274 would not be torn completely away from first part 272. However, the fold or bend line in FIG. 8 could be formed to include such holes 276; in such an embodiment, second part 274 could be completely torn away from first part along such holes 276. Covering 223 can be made of polyethylene, polypropylene, or polystyrene, for example.

In use, chemical delivery assembly 210 is removed from the enclosure. In so doing, the in-rush of air through the holes in bottom wall 126 of housing element 116 causes heating element 114 to become heated. Second part 274 of covering 223 is peeled back along holes 276. The heating of chemical storage device 112 causes volatilized chemical 118 to be emitted into ambient environment 115 about chemical delivery assembly 210.

Figure 10:
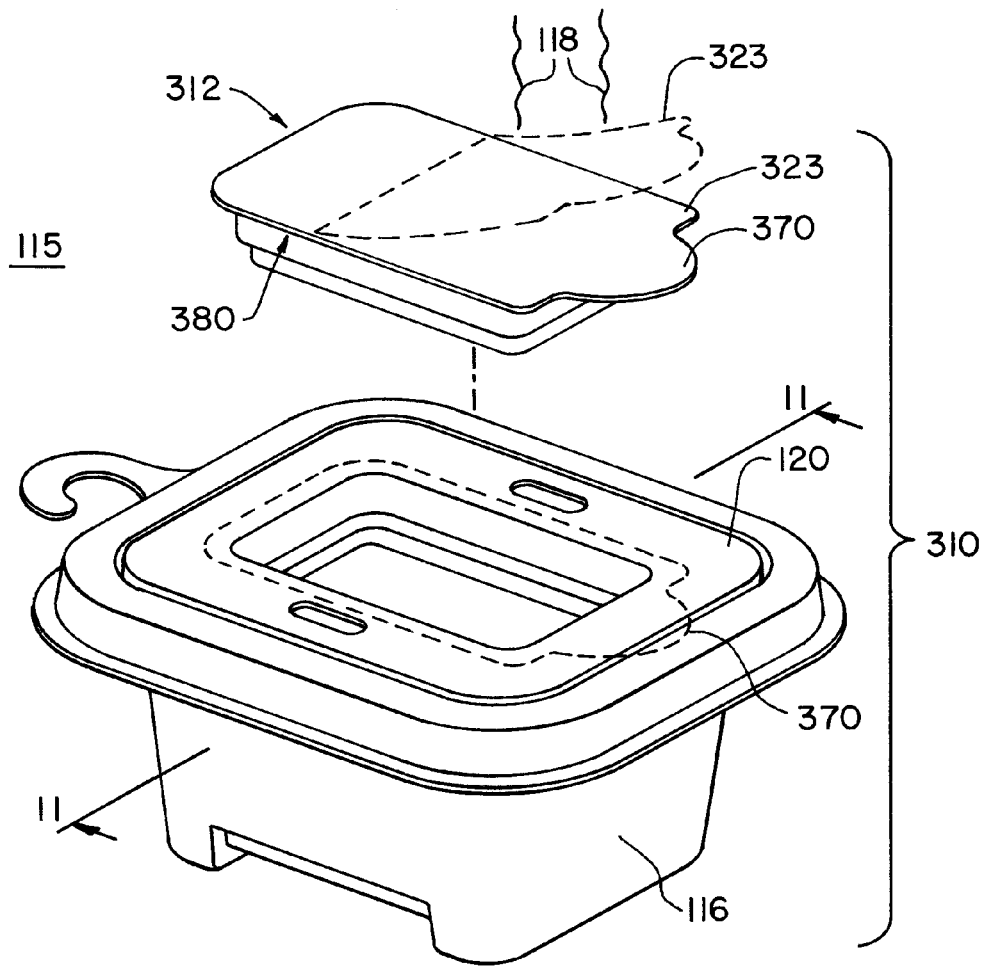
FIG. 10 is an exploded, perspective view of yet another embodiment of the chemical delivery assembly according to the present invention.
Figure 11:
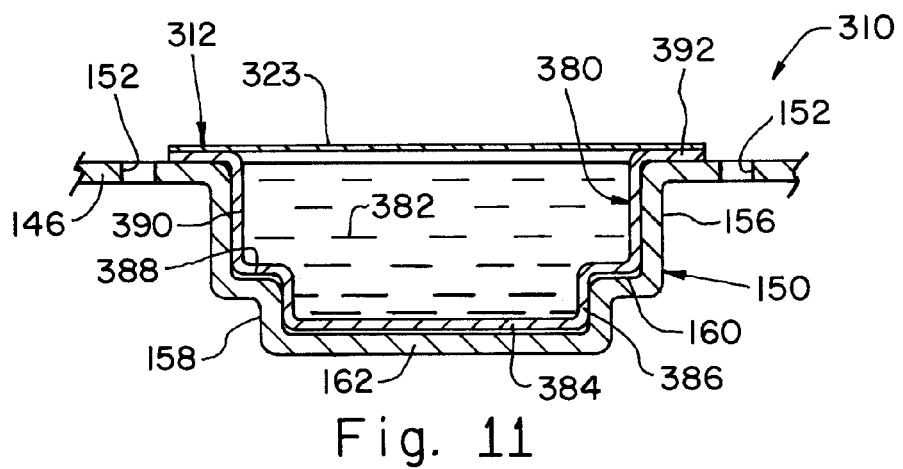
FIG. 11 is a sectional view of part of the chemical delivery assembly of FIG. 10 taken along line 11-11.

Now, additionally referring to FIGS. 10 and 11, there is shown yet another embodiment of the chemical delivery assembly of the present invention, that assembly having the reference number 310. Like chemical delivery assembly 110, chemical delivery assembly 210 is used in conjunction with an enclosure 109 (i.e., a bag), chemical delivery assembly 310 and enclosure 109 being parts of a chemical delivery system; enclosure 109 is thus not shown in FIGS. 10-11. Chemical delivery assembly 310 is the same as chemical delivery assembly 110 in all respects except that chemical delivery assembly does not include retainer 122 or the same chemical storage device 112; thus, many of the structural components of chemical delivery assembly 310 have the same reference characters as those of chemical delivery assembly 110. Rather than including chemical storage device 112, chemical delivery assembly 310 includes chemical storage device 312.

Chemical storage device 312 is a removable hermetically sealed packet which is frictionally attached to well 150. Chemical storage device 312 can also be referred to as packet or gel packet 312. Packet 312 includes a body 380, a gel 382 with the volatilizable chemical, and a peelable covering 323. Body 380 is snap-fitted to and matingly received by well 150. Body 380 has an outer contour which matches the inner contour of well 150. Body 380 frictionally fits, using an interference fit, with well 150 and thus can be said to snap-fit or snap-in to well 150. Body 380 includes a bottom wall 384, a fifth plurality of vertical walls 386 coupled to one another and extending upwardly relative to bottom wall 384, a horizontal shoulder 388 extending radially outwardly from the top of fifth plurality of vertical walls 386, a sixth plurality of vertical walls 390 extending upwardly relative to an outer radial extent of horizontal shoulder 388, and a horizontal ledge 392 running radially outwardly from the top of sixth plurality of vertical walls 390. Thus, when body 380 is matingly received by well 150, bottom wall 384 is adjacent bottom wall 162 of well 150, vertical walls 386 are adjacent vertical walls 158 of well 150, horizontal shoulder 388 is adjacent horizontal shoulder 160 of well 150, vertical walls 390 are adjacent vertical walls 156 of well 150, and horizontal ledge 392 is adjacent top horizontal wall 146 of lid 120. Thus, vertical walls 386 and vertical walls 158 form an interference fit relative to one another, and/or vertical walls 390 and vertical walls 156 form an interference fit relative to one another. Peelable covering 323 is attached to body 380 by, for example, an adhesive. More specifically, peelable covering 323 is attached to the upper surface of horizontal ledge 392. Peelable covering 323 includes a tab 370. Peelable covering 323 is configured for being removed from body 380, using tab 370, to thereby emit volatilized chemical 118 to ambient environment 115. Peelable covering 323 can be a peelable foil seal. FIG. 10 shows packet 312 in solid lines exploded from lid 120. FIG. 10 also shows packet 312 in broken lines attached to lid 120. The packet 312 which is in solid lines and exploded from lid 120 in FIG. 10 is also shown as having covering 323 in solid lines affixed to body 380 and also in broken lines partially torn away from body 380. FIG. 11 shows packet 312 friction fit to well 150.

In use, chemical delivery assembly 310 is removed from the enclosure. In so doing, the in-rush of air through the holes in bottom wall 126 of housing element 116 causes heating element 114 to become heated. Peelable covering 323 is peeled off of body 380. The heating of gel 382 in body 380 causes volatilized chemical 118 to be emitted into ambient environment 115 about chemical delivery assembly 310. When no meaningful amount of volatilized chemical 118 is emitted from packet 312, the used packet 312 can be removed from lid 120, and a new unused packet 312 can be inserted in well 150 and snap-fit thereto. Gel packet 312 can be used, for example and not by way of limitation, as a game lure or as an insecticide.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A chemical delivery system, comprising:
a chemical storage device configured for emitting a volatilized chemical therefrom;
a heating element which provides an exothermic chemical reaction;
an at least substantially rigid exterior housing element including a top portion and containing said heating element; and
a lid including a first horizontal wall, a first plurality of vertical walls coupled to one another and depending downwardly from said first horizontal wall, and a well spaced radially inwardly relative to said first plurality of vertical walls and depending downwardly from said first horizontal wall, said chemical storage device being mounted to said well, said heating element being in thermal communication with said chemical storage device via said well, said first plurality of vertical walls being attached to only said top portion of said housing element, said chemical storage device being a removable hermetically sealed packet which is frictionally attached to said well, said packet including a peelable covering configured for being removed to thereby emit said volatilized chemical to an ambient environment, said packet including a gel, said well including a second plurality of vertical walls coupled to one another and spaced radially inwardly relative to said first plurality of vertical walls and depending downwardly from said first horizontal wall, a third plurality of vertical walls coupled to one another and spaced radially inwardly relative to said second plurality of vertical walls, a horizontal shoulder coupling said second plurality of vertical walls with said third plurality of vertical walls, and a second horizontal wall connected to said third plurality of vertical walls, said packet including a body to which said peelable covering is attached, said body being snap-fitted to and matingly received by said well.

2. The chemical delivery system of claim 1, wherein said well has an absence of a through-hole.

\* \* \* \* \*